United States Patent [19]

Dinu et al.

[11] Patent Number: 4,689,347
[45] Date of Patent: Aug. 25, 1987

[54] MEDICINAL COMPOSITION FOR THE TREATMENT OF CERTAIN NEUROVIRUSES

[75] Inventors: Romulus C. Dinu; Illeana D. Dinu, both of Bucharest, Romania

[73] Assignee: Centrala Industriala de Medicamente Cosmetice Coloranti Si Lacuri, Bucharest, Romania

[21] Appl. No.: 786,703

[22] PCT Filed: Dec. 8, 1982

[86] PCT No.: PCT/RO82/00007

§ 371 Date: Aug. 18, 1983

§ 102(e) Date: Aug. 18, 1983

[87] PCT Pub. No.: WO83/02893

PCT Pub. Date: Sep. 1, 1983

Related U.S. Application Data

[63] Continuation of Ser. No. 705,040, Feb. 25, 1985, abandoned, which is a continuation of Ser. No. 527,575, Aug. 18, 1983, abandoned.

[30] Foreign Application Priority Data

Feb. 23, 1982 [RO] Romania .............................. 106709

[51] Int. Cl.$^4$ .................... A61K 31/19; A61K 31/195
[52] U.S. Cl. .................... 514/557; 514/562; 514/566; 514/934
[58] Field of Search ................ 514/557, 562, 566, 934

[56] References Cited

U.S. PATENT DOCUMENTS 4,390,525 6/1983 Yoshioka et al. .................... 424/71

FOREIGN PATENT DOCUMENTS 687563 2/1940 Fed. Rep. of Germany .
1550706 8/1979 United Kingdom .

OTHER PUBLICATIONS

Chem. Abstracts, vol. 87, 1977, 148503h, Citation of Marcialis et al., Experientia, 1977 33(8), 1044-5.
Perrin et al., Pharmac. Ther. 22, pp. 255, 268, 281, 282, 286 and 289 (1981).

*Primary Examiner*—Johnnie R. Brown
*Assistant Examiner*—Jacqueline M. Stone
*Attorney, Agent, or Firm*—Karl F. Ross; Jonathan Myers; Herbert Dubno

[57] ABSTRACT

A new pharmaceutical composition is disclosed useful in the treatment of neuroviruses and formulated as an injectable solution. The pharmaceutical composition is composed of the calcium and sodium double salt of ethylene diamine tetracetic acid, associated with calcium gluconate as a source of $Ca^{2+}$ ions, and cysteine or its HCl salt, wherein the weight ratio of the ingredients ranges from 8-12 g to 0.3 to 1 g to 0.05 to 0.2 g respectively per 100 ml of water.

1 Claim, No Drawings

MEDICINAL COMPOSITION FOR THE TREATMENT OF CERTAIN NEUROVIRUSES

CROSS REFERENCE TO RELATED APPLICATIONS

This application is a continuation of Ser. No. 705,040 filed Feb. 25, 1985, now abandoned, which was a continuation of Ser. No. 527,575, filed Aug. 18, 1983, now abandoned.

FIELD OF THE INVENTION

The present invention relates to a medicinal composition for the treatment of neuroviruses, specifically herpes Zoster and herpes (herpes Simplex).

BACKGROUND OF THE INVENTION

Certain pharmeceutical compositions are known to be effective against herpes Zoster; the antibiotic Rifamycin or the immune stimulating agent Isoprinosine (Lesourd B, Loude, J., Meunier, P., Doumerc, P., Moulias, R., Traitement du zona ZOSTER par Isoprinosine, La nouv. Presse Medicale, Jan. 23 1982, II, No. 3, p. 191) and other chemotherapeutic compounds such as idoxuridine (Juel Jensen B.E., Treatment of Zoster with Idoxuridine in Dimethylsulfoxide; Result of Two Blind Control Trials; Brit. Med. J. 1970 (4), pp 776–780; cytosine arabinoside (Pierle, l.N., Cytosine Arabinoside for Herpes Zoster, New Eng. J. Med., 1974,290, pp 404–410) and adenine arabinoside (Whitely, R.J. et al, Adenine Arabinoside Therapy for Herpes Zoster, New Eng. J. Med., 1976, 294, pp 1193–1199).

Isoprinoside has a slow curvature action upon Zoster eruption; its effect upon pain is practically insignificant. The other substances, idoxuridine, cytosine, arabinoside, and adenine arabinoside are contraindicated on account of side effects.

The antivirotic action of several classes of chelators has been ascertained as against a large spectrum of viruses (Perrin D.D. and Stünzi H., 1981 - Pharmac.-Ther.22, 255) in in vitro studies or in animal studies; even certain compounds of the class of thiosemicarbazones were proved to be active in the prophylaxis of chicken pox in an epidemic in Madras. In our country. Gh.D.Grigorescu wrote (in 1955) that dimercaptopropanol (DMP; BAL) is effective against herpes Zoster and against some other viroses (1973); however, DMP is not indicated for human use to the fact that the therapeutic dose is higher than the toxic dose (L.Goodman, The Pharmacological Basis of Therapeutics,1980 Ed.L.Goodman, A.Gilman).

The detoxifying action of the ethylene diamino-tetracetic acid is well-known; this product is used as an antidote in poisonings with bi and trivalent metals; its mechanism of action is explained by a chelating process.

The chelating action of the ethylene diaminotetracetic acid and of its salts with various metal ions is dependent upon temperature, pH, and the specific activity of the chelating agent expressed by the stability constant of the resulting complex.

Its antiviral effect has only been proved in in vitro studies on some viral enzymes—the polymerases of viral nucleic acids and the neuraminidase of the A flu virus (Perrin D.D. and Stünzi H., 1981, Pharmac.-Ther.22, 255)—whose activity was inhibited by the ethylenediaminotetracetic acids thus, viruses multiplication and their penetration into cells was prevented; however, this chelator has not been as yet used in antiviral human therapy.

The prior art does not mention pharmaceuticals or medicinal compositions meant for antiviral therapy with the ethylene diamino tetracetic acid as their active ingredient.

DISCLOSURE OF INVENTION

The composition as per the present invention, formulated as injectable solution, contains the calcium and sodium salt of ethylene diamino tetracetic acid, associated with calcium gluconate as a source of $Ca^{2+}$ ions and an aminoacid (preferably cysteine) or a tripeptide (glutathion); the association ratio of the 3 ingredients is 8 ... 12; 0.3 ... 1; 0.05 ... 0.2.

The advantages of the preparation as per the invention are the following:

the drug has a specific effect in treating herpes Zoster, and herpes (Herpes Simplex).

the use of cysteine and the ethylene diamino tetracetic acid in the form of its double salt of calcium and sodium as chelating agents provides an anti-inflammatory and trophic and antiviral effect, ensures a rapid diffusion as well as a uniform distribution in the tissues. Since it is not metabolized in the organism, the product is rapidly eliminated (50% within the first hour from i.p. administration and 100% within 24 hours in rats).

the Na and Ca double salt of the ethylene diaminotetracetic acid and cysteine are toxity - free in the dosage prescribed for the above mentioned neurovirotic disorders.

See below 2 concrete examples:

EXAMPLE 1

The composition of active ingredients for 100 ml of injectable solution as per the invention is the following:

| | |
|---|---|
| Calcium and sodium salt of the ethylenediamino tetracetic acid | 10 g |
| Calcium gluconate | 0.5 g |
| Cysteine hydrochloride | 0.1 g |
| Distilled water ad | 100 ml |

In about 80 ml of fresh distilled water, dissolve, at 80° C., the calcium and sodium salt of the ethylenediamino tetracetic acid and then 0.5 g of calcium glüconate and 0.1 g of cysteine hydrochloride; add distilled water to 100 ml, then filter through a Millipere filter.

Divide the filtered solution in colorless 10 ml ampoules; sterilize by keeping in the autoclave at 120° C., for 30 minutes.

EXAMPLE 2

The composition of active ingredients for 100 ml of injectable solution as per the invention is the following:

| | |
|---|---|
| Calcium and sodium salt of the ethylenediamino tetracetic acid | 10 g |
| Calcium gluconate | 0.5 g |
| Glutathion | 0.05 g |
| Distilled water ad | 100 ml |

In about 80 ml of fresh distilled water, dissolve at 80° C. the calcium and sodium salt of the ethylenediamino tetracetic acid, and then 0.5 g of calcium gluconate, then add the glutathion, previously dissolved in 5 ml of distilled water. Add water to 100 ml and filter through a Millipore filter.

Divide the filtered solution in colorless 10 ml ampoules; sterilize by keeping in the autoclave at 120° C. for 30 minutes.

The injectable solution as per the invention should be intramuscularly administered, 10 ml in 24 hours, over a period 6-7 days.

The hypotheses on the mechanism of action of the pharmaceutical preparation as per this invention are based on several recent studies that have proved that the metal ions in the organism are both directly and indirectly involved in the synthesis and metabolism of proteins and viral nucleic acids. The chelation of several such ions by the chelators in this preparation inhibits viruses multiplication through the modification of the metal ions balance.

Beside hindering the process of virus multiplication, the chelators in the claimed pharmaceutical prepartion, also act in viral and autoimmune disorders—such as multiple sclerosis whose etiopathology is still unknown; they determine the fluctuation of plasma $Ca^{2+}$, thus restoring certain lesions of the cell membrane and implicity, certain neuronal activities. Consequently, the drug may be also effective in checking such autoaggressive processes.

The association of cysteine to ethylenediamino tetracetic acid has a synergistic effect upon the latter's chelating action, since cysteine itself has the ability to fixate electrophilic agents (cations) bu the thiolic group. Moreover, cysteine has the property to form, with some transition metals, slightly soluble complex combinations in which the nitrogen atom is coordinatively linked to the metal.

The initial experiments on the effect of the ethylenediamino tetracetic acid associated with calcium gluconate upon certain neuroviruses have only pointed out a temporary restoring of the nervous influx; the association with cysteine has resulted in a long-lasting remission of paralysis in multiple sclerosis, a strong anti-inflammatory and trophic effect and an intensifying of the antiviral action.

Moreover, cysteine may reduce the mutagenic effect of some chemical compounds (M.Moriya, K.Kato, Y.-Shirasu, Mutation Research 1978, 57, 259) and therefore prevents the mutagenic effect of the pharmaceutical preparation.

Reduced glutathion (γ- glutamyl-cystenyl-glycine) is a natural tripeptide to be found in all animal and vegetable tissues; it is involved in the organism's defense mechanisms and considered to have an anti-mutagenic effect by protecting the nucleophilic groups, from informational macromoleculas (DNA) against strongly electrophilic agents.

Glutathion capacity to fixate through its thiolic groups, electrophilic agents (metal cations) may be compared to a chelation mechanism.

Thus, by associating glutathion to the ethylenediamino tetracetic acid, the chelating capacity of the latter is completed and enhanced and the product is provided with an antimutagenic action.

In the structure of glutathion, an abnormal peptidic link can be noticed, which is similar to the structure of certain natural very strong antibiotics (produced by bacteria) and which are considered to be endowed with an antiviral property.

Unlikely such antibiotics which are highly toxic glutathion, which is a normal multifunctional metabolite of the Human organism, and is devoid of toxicity.

We claim:

1. A pharmaceutical composition in the form of an aqueous injectable solution for the treatment of Herpes Zoster or Herpes Simplex said composition consisting essentially of:
   (a) the calcium and sodium double salt of ethylenediamine tetracetic acid;
   (b) calcium gluconate; and
   (c) cysteine or its HCl salt, wherein the weight ratio of the ingredients ranges from 8-12 g to 0.3 to 1 g to 0.05 to 0.2 g respectively per 100 ml of water.

* * * * *